United States Patent [19]

Glamkowski et al.

[11] Patent Number: 5,189,161
[45] Date of Patent: Feb. 23, 1993

[54] BENZO(B)PYRROLOBENZODIAZEPINES

[75] Inventors: Edward J. Glamkowski, Warren; Barbara E. Kurys, Elmwood Park, both of N.J.

[73] Assignee: Hoechst Roussel Pharmaceuticals Inc., Somerville, N.J.

[21] Appl. No.: 663,352

[22] Filed: Mar. 4, 1991

Related U.S. Application Data

[62] Division of Ser. No. 586,357, Sep. 21, 1990, Pat. No. 5,015,738, which is a division of Ser. No. 390,130, Aug. 7, 1989, Pat. No. 4,983,601.

[51] Int. Cl.$^5$ .......................................... C07D 243/14
[52] U.S. Cl. ................................... 540/555; 540/556
[58] Field of Search ................................ 540/555, 556

[56] References Cited

U.S. PATENT DOCUMENTS

| | | | |
|---|---|---|---|
| 3,534,041 | 10/1970 | van der Berg | 540/579 |
| 3,862,950 | 1/1975 | Szmuskovitz | 540/555 |
| 3,956,297 | 5/1976 | Gall | 540/555 |
| 4,186,199 | 1/1980 | Glamkowski et al. | 424/232 |
| 4,192,874 | 3/1980 | Glamkowski et al. | 424/248.54 |
| 4,472,414 | 9/1984 | Glamkowski et al. | 424/267 |
| 4,663,453 | 5/1987 | Glamkowski et al. | 540/556 |
| 4,751,223 | 6/1988 | Glamkowski et al. | 514/219 |

FOREIGN PATENT DOCUMENTS 2301399 8/1973 Fed. Rep. of Germany .
1384991 2/1975 United Kingdom .

OTHER PUBLICATIONS

K. Hofmann, Chemistry of Heterocyclic Compounds Inter Science Publisher Inc. New York, 1953, pp. 235–237.

E. J. Glamkowski, et al., J. Heterocyclic Chem., 16, 865 (1979).

*Primary Examiner*—Mukund J. Shah
*Assistant Examiner*—Yogendra N. Gupta
*Attorney, Agent, or Firm*—Raymond R. Wittekind

[57] ABSTRACT

Novel benzo[b]pyrrolo[3,2,1-jk]benzodiazepines, intermediates and processes for the preparation thereof, and methods for alleviating pain utilizing the compounds or compositions thereof are disclosed.

22 Claims, No Drawings

BENZO(B)PYRROLOBENZODIAZEPINES

This is a division of application Ser. No. 586,357 filed Sep. 21, 1990 now U.S. Pat. No. 5,015,738, which is a division of application Ser. No. 390,130 filed Aug. 7, 1989 now U.S. Pat. No. 4,983,601.

The present invention relates to benzo[b]pyrrolo[3,2,1-jk]benzodiazepines. More particularly, the present invention relates imidazo-, triazolo-, and tetrazolobenzo[b]pyrrolo[3,2,1-jk]benzodiazepines of the formula

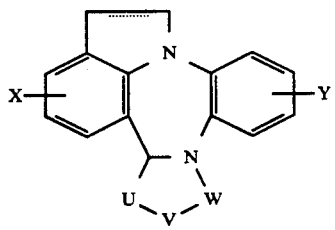

wherein U—V—W is —N—N=CR, $NR^1$—N=$CR^2$, —N—$NR^3$—C=O, —N—N=N, $CH_2$—$NR^4$—C=Z, or —N—C=C—$R^5$ wherein R is hydrogen, loweralkyl, $CONH_2$, $CH_2OH$, $CH_2Cl$,

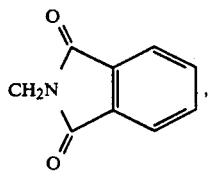

or a group of the formula $(CH_2)_m NR^6 R^7$ wherein $R^6$ and $R^7$ are independently hydrogen, loweralkyl, loweralkenyl, phenethyl, cycloalkylmethyl or cycloalkylcarbonyl; and $R^6$ and $R^7$ taken together with the nitrogen atom to which they are attached form a group of the formula

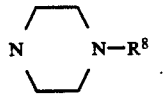

wherein $R^8$ is loweralkyl; $R^1$ and $R^2$ are phenyl; $R^3$ is hydrogen, cycloalkylmethyl, loweralkenyl, phenethyl, a group of the formula $(CH_2)_n R^9$ wherein $R^9$ is $NR^{10}R^{11}$ wherein $R^{10}$ and $R^{11}$ are independently loweralkyl, a group of the formula

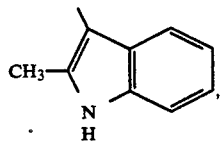

a group of the formula

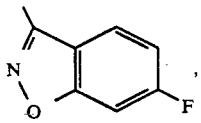

or a group of the formula

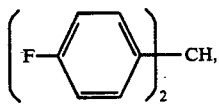

m and n are independently 1, 2 or 3; $R^4$ is hydrogen or loweralkyl and Z is O or S; $R^5$ is loweralkyl; X and Y are independently hydrogen, loweralkyl, or halogen; the dotted line represents an optional carbon-to-carbon bond; an optical or geometrical isomer thereof, or a pharmaceutically acceptable acid addition salt thereof, which are useful for alleviating pain alone or in combination with adjuvants.

Subgeneric to the benzo[b]pyrrolo[3,2,1-jk]benzodiazepines of the present invention are compounds wherein:
(a) wherein U—V—W is —N—N=CR;
(b) wherein U—V—W is —$NR^1$—N=$CR^2$;
(c) wherein U—V—W is —N—$NR^3$—C=O;
(d) wherein U—V—W is —N—N=N;
(e) wherein U—V—W is $CH_2$—$NR^4$—C=Z;
(f) wherein U—V—W is —N—C=C—$R^5$.

The present invention also relates to benzo[b]pyrrolo[3,2,1-jk][1,4]benzodiazepinones, -thiones, and -hydrazones of the formula

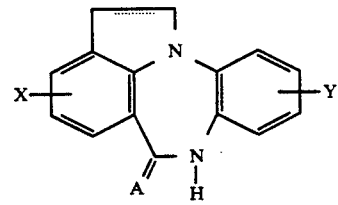

wherein A is S, O, or $NNH_2$; and X and Y are independently hydrogen, loweralkyl, or halogen; and the dotted line represents an optional carbon-to-carbon bond, or an optical isomer thereof, which are useful as intermediates for the synthesis of the present benzo[b]pyrrolo[3,2,1-jk]benzodiazepines.

As used throughout the specification and appended claims, the term "alkyl" refers to a straight or branched chain hydrocarbon radical containing no unsaturation and having 1 to 8 carbon atoms such as methyl, ethyl, 1-propyl, 2-propyl, 1butyl, 1-pentyl, 2-pentyl, 3-hexyl, 4-heptyl, 2-octyl, and the like; the term "alkenyl" refers to a straight or branched chain hydrocarbon radical containing unsaturation in the form of a single carbon to carbon double bond and having from 2 to 8 carbon atoms such as propenyl, 2-butenyl, 2-methyl-2-butenyl, 3-hexenyl, 3-ethyl-2-pentenyl, 3-methyl-3-heptenyl, octenyl, and the like; the term "cycloalkyl" refers to a saturated hydrocarbon group possessing at least one carbocyclic ring, the ring containing from 3 to 8 carbon atoms such as cyclopropyl, cyclobutyl, cyclopentyl, cyclohexyl, cycloheptyl, cyclooctyl, and the like; the term "alkanol" refers to a compound formed by a combination of an alkyl group and a hydroxy radical such as methanol, ethanol, 1-and 2-propanol, 1,2-dimethylethanol, hexanol, octanol and the like; the term "halogen" refers to a member of the family consisting of fluorine, chlorine, bromine or iodine. The term "lower" as applied to any of the aforementioned groups refers to a group having a carbon skeleton containing up to and including 6 carbon atoms.

The compounds of the present invention which lack an element of symmetry exist as optical antipodes and as the racemic forms thereof. Optical antipodes may be prepared from the corresponding racemic forms by standard optical resolution techniques, involving, for example, the separation of diasteromeric salts of those instant compounds characterized by the presence of a basic amino group and an optically active acid, or by the synthesis from optically active precursors.

The present invention comprehends all optical isomers and racemic forms thereof and all geometric isomers of the compounds disclosed and claimed herein. The formulas of the compounds shown herein are intended to encompass all possible optical isomers of the compounds so depicted.

The novel benzo[b]pyrrolobenzodiazepines of the present invention are prepared by processes illustrated in Reaction Schemes A, B, and C.

To gain entry into the benzo[b]pyrrolo[3,2,1-jk][1,2,4]triazolo[4,3-d][1,4]benzodiazepine system, i.e., to prepare compounds of formula 3, a benzo[b]pyrrolo[3,2,1-jk][1,4]benzodiazepin-6-one 1, the synthesis of which is described in U.S. Pat. No. 4,663,453 issued May 5, 1987, is thiated to a benzo[b]pyrrolo[3,2,1-jk][1,4]benzodiazepin-6-thione 2, which is converted to a benzo[b]pyrrolo[3,2,1-jk][1,2,4]triazolo[4,3-d][1,4]benzodiazepine 3.

The thiation of a benzodiazepinone 1 to the corresponding thione 2 is conveniently accomplished by contacting a diazepinone 1 with commercially available 2,4-bis(4-methoxyphenyl)-1,3-dithia-2,4-diphosphetane-2,4-disulfide (Lawesson's reagent) in an aromatic solvent such as, for example, benzene, toluene, xylene, and the like, toluene being preferred. The reaction temperature is not narrowly critical; a reaction temperature of about the reflux temperature of the medium is preferred to assure a reasonable rate of thiation.

The conversion of a benzodiazepinthione 2 to a triazolobenzodiazepine 3 is performed by reacting a thione 2 with an acylhydrazine of the formula

H$_2$NNHCR

8 wherein R is hydrogen, alkyl, a group of the formula CONH$_2$ or a group of the formula (CH$_2$)$_m$NR$^6$R$^7$ wherein R$^6$ and R$^7$ are independently hydrogen or alkyl and m is 2 or 3; and R$^6$ and R$^7$ taken together with the nitrogen atom to which they are attached form a group of the formula

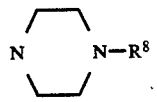

wherein R$^8$ is alkyl to provide triazolobenzodiazepine 3 wherein R is as immediately above in a suitable solvent.

Among suitable solvents, one may mention alkanols such as methanol, ethanol, 2-propanol, 1-butanol, and the like, and aprotic dipolar solvents such as dimethylacetamide, dimethylformamide, dimethylsulfoxide, and hexamethylphosphoramide. 1-Butanol and dimethylformamide are the preferred solvents. The conversion is generally carried out at about the reflux temperature of the reaction medium, although it proceeds readily at moderate temperatures.

Alternatively, to prepare triazolobenzodiazepine 3 wherein R is hydrogen, one employs hydrazine in excess dimethylformamide, the formamide acting as both a reactant and solvent, under conditions substantially similar to those described hereinbefore for the transformation of 2 to 3.

To fabricate a triazolobenzodiazepine 3 wherein R is CH$_2$OH, CH$_2$Cl, alkenyl, or a group of the formula CH$_2$NR$^6$R$^7$ wherein R$^6$ and R$^7$ are hydrogen, alkyl, alkenyl, cycloalkyl, or phenethyl, a trizaolobenzodiazepine 3, i.e., a diazepine 3 wherein R is hydrogen, is condensed with formaldehyde, or an equivalent thereof such as paraformaldehyde, in an aromatic solvent, for example, benzene, toluene or xylene, xylene being preferred, at the reflux temperature of the reaction medium to provide a hydroxymethyltriazolobenzodiazepine 5. The benzodiazepine 5 is then converted to an aminoalkyltriazolobenzodiazepine 7 wherein R$^6$ and R$^7$ are as above, either directly or with isolation of an intermediate chloromethyltriazolobenzodiazepine 4. Thus, treatment of hydroxymethyltriazolobenzodiazepine 5 with methanesulfonyl chloride or p-toluenesulfonyl chloride in a halocarbon, (e.g., dichloromethane, trichloromethane, 1,2-dichloroethane and the like, in the presence of an acid acceptor, for example, a trialkylamine such as triethylamine at about ambient temperature provides an isolable chloromethyltriazolobenzodiazepine 4, which upon contact with an amine of the formula

HNR$^6$R$^7$           9 wherein R$^6$ is hydrogen and R$^7$ is hydrogen, alkenyl or cycloalkyl in a dipolar aprotic solvent, e.g., dimethylacetamide, dimethylformamide, hexamethylphosphoramide, or dimethylsulfoxide in the presence or absence of a catalyst such as an alkali metal bromide or iodide, e.g., sodium or potassium bromide or iodide, at about ambient temperature affords aminoalkyltriazolobenzodiazepine 7 wherein R$^6$ and R$^7$ are as immediately above.

Similarly, treatment of hydroxymethyltriazolobenzodiazepine 5 with methanesulfonyl or p-toluenesulfonyl chloride in a halocarbon solvent in the presence of an acid acceptor followed by an amine 9 wherein R$^6$ is hydrogen and R$^7$ is alkyl or phenethyl, without isolation of the intermediate chloromethyltriazolobenzodiazepine 4, yields aminomethyltriazolobenzodiazepine 7 wherein R$^6$ and R$^7$ are as immediately above.

To prepare an acyl derivative of aminomethylbenzodiazepine 7 (e.g., a benzodiazepine 7 wherein R$^6$ is alkyl and R$^7$ is cycloalkylcarbonyl), an aminomethylbenzodiazepine 7 wherein R$^6$ is alkyl and R$^7$ is hydrogen is condensed with a cycloalkylcarbonyl halide of the formula R$^{12}$COHal           10 wherein R$^{12}$ is cycloalkyl and Hal is chloro or bromo in a suitable solvent such as acetonitrile in the presence of an acid acceptor such as an alkali metal carbonate, e.g., sodium carbonate or potassium carbonate, potassium carbonate being preferred. The condensation proceeds readily at about ambient temperature to the reflux temperature of the reaction medium, the reflux temperature of the reaction medium being preferred to accelerate the transformation.

To prepare an arylalkylaminomethylbenzodiazepine 7 (e.g., a benzodiazepine 7 wherein $R^6$ is alkyl and $R^7$ is phenethyl), an aminomethylbenzodiazepine 7 wherein $R^6$ is alkyl and $R^7$ is hydrogen is condensed with an aralkyl halide of the formula $R^6Hal$  10a wherein $R^6$ is phenethyl and Hal is chloro or bromo under reaction conditions substantially the same as those employed for the acylation of 7.

An aminomethyltriazolobenzodiazepine 3, i.e., a benzodiazepine 7 wherein $R^6$ and $R^7$ are hydrogen is synthesized by condensing a chloromethyltriazolobenzodiazepine 4 with potassium phthalimide to provide a phthalimidomethyltriazolobenzodiazepine 7 where $R^6$ and $R^7$ taken together with the nitrogen atom to which they are attached form a group of the formula

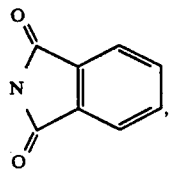

which is cleaved to an aminomethyltriazolobenzodiazepine 3. The condensation is typically accomplished in a dipolar aprotic solvent, for example, dimethylformamide at about ambient temperature. The cleavage of the resultant phthalimidomethyltriazolobenzodiazepine 7 is generally accomplished by means of hydrazine as the hydrate in an alkanol, for example, methanol, at about ambient temperature.

The synthesis of 7-substituted-triazolobenzodiazepinones 12 is effected by condensing a benzo[b]pyrrolo[3,2,1-jk][1,4]benzodiazepin-6-thione 2 with an alkyl carbazate of the formula

   13 wherein $R^{13}$ is alkyl to form a triazolobenzodiazepinone 11, which is alkylated with a halide of the formula $R^3Hal$   14 wherein $R^3$ is cycloalkylmethyl, alkenyl, phenethyl, a group of the formula $(CH_2)_nR^9$ wherein $R^9$ is $NR^{10}R^{11}$ wherein $R^{10}$ and $R^{11}$ are independently alkyl, a group of the formula

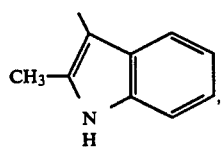

a group of the formula

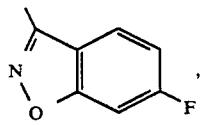

or a group of the formula

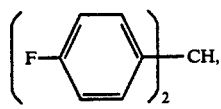

and n is 2 or 3.

The condensation of a diazepin-6-thione 2 with an alkyl carbazate 13 is generally accomplished by heating a mixture of the reactants at an elevated temperature of about 150° to about 250° C., a reaction temperature of about 195°–200° C. being preferred.

The alkylation is typically performed in an dipolar aprotic solvent, for example, dimethylacetamide, dimethylformamide, hexamethylphosphoramide, dimethylsulfoxide, and the like, or a mixture of a dipolar aprotic solvent and an aromatic solvent, for example, benzene, toluene, xylene, and the like, in the presence of a base such as an alkali metal carbonate, e.g., sodium or potassium carbonate, or an alkali metal hydride, e.g., lithium or sodium hydride at a reaction temperature of about 50° to 125° C. Dimethylformamide is the preferred solvent, and when a combination of solvents is employed, a mixture of dimethylformamide and xylene is preferred. Potassium carbonate and sodium hydride are the preferred bases, and a temperature within the range of about 95°–100° is the preferred reaction temperature.

A triazolobenzodiazepine 16 is prepared by treating a benzo[b]pyrrolo[3,2,1-jk][1,4]benzodiazepine 15, the synthesis of which is described in E. J. Glamkowski and J. M. Fortunato, J. Heterocyclic Chem., 16, 865 (1979), with bis-phenylhydrazidoyl chloride in an aromatic solvent in the presence of an acid acceptor. Among aromatic solvents, there may be mentioned benzene, toluene, xylene, and the like. Benzene is the preferred solvent. Among acid acceptors, there may be mentioned trialkylamines, e.g., trimethylamine, triethylamine, tri-(2-propyl)amine, and the like. Triethylamine is preferred. While the reaction temperature is not critical, a temperature of about the reflux temperatures of the reaction medium is typically employed.

To provide entry into the tetrazolobenzodiazepine series, i.e., to provide tetrazolobenzodiazepines 18, a benzo[b]pyrrolo[3,2,1-jk][1,4]benzodiazepin-6-thione 2 is converted to a hydrazonobenzodiazepine 17, which is aminated and cyclized in situ to afford tetrazolobenzodiazepine 18. The conversion of 2 to 17 is conveniently carried out by treating a thione 2 with hydrazine or its hydrate in an aromatic solvent, e.g., benzene, toluene, xylene, and the like, benzene being preferred, at the reflux temperature of the reaction medium, although reduced temperatures may be employed. The amination-cyclization, i.e., the conversion of hydrazonobenzodiazepine 17 to tetrazolobenzodiazepine 18, is generally performed by contacting a hydrazone 17 with an alkali metal nitrite, e.g., sodium or potassium nitrite, and a mineral acid, e.g., hydrochloric acid or hydrobromic acid, at about ambient temperature or at a moderately elevated temperature within the range of from about ambient to 50° C. A reaction system of sodium nitrite and hydrochloric acid is preferred. A reaction temperature of about ambient temperature is also preferred.

Imidazobenzodiazepines 19 are constructed from thiones 2 by cyclizing a thione 2 with a propargyl amine of the formula

$$R^{14}-C\equiv C-CH_2NH_2 \qquad 22$$

wherein $R^{14}$ is hydrogen, alkyl, or phenyl. Thus, treatment of a thione 2 with a propargyl amine 22 in an alkanol, e.g., methanol, ethanol, 2-propanol, 1-butanol, or the like, in the presence of an organic acid, i.e., a sulfonic acid, e.g., methanesulfonic or p-toluenesulfonic acid, at an elevated temperature, e.g., about the reflux temperature of the reaction medium provides an imidazobenzodiazepine 19. 1-Butanol and p-toluenesulfonic acid at about the reflux temperature of the reaction medium are the preferred reaction conditions.

Imidazobenzodiazepinones and -thiones 21 wherein Z is oxygen or sulfur are fabricated by contacting a 6-aminomethylbenzodiazepine 20, the preparation of which is described in U.S. Pat. No. 4,751,223 issued Jun. 14, 1988, with phosgene or carbon disulfide, respectively. The cyclization of aminomethylbenzodiazepine 20 with phosgene is typically accomplished in a halocarbon solvent in the presence of an acid acceptor. Halocarbon solvents include dichloromethane, trichloromethane, and the like. Acid acceptors include alkali metal carbonates, e.g., sodium or potassium carbonate. Dichloromethane and potassium carbonate are preferred. The cyclization is conveniently performed at a reduced temperature within the range of about −25° to 5° C., a temperature of about 0° C. is preferred.

The cyclization of aminomethylbenzodiazepine 20 with carbon disulfide is generally effected in an alkanol, e.g., methanol, ethanol, 2-propanol, and the like, 95% ethanol being preferred, at about the reflux temperature of the reaction medium.

Imidazobenzodiazepinones 21 wherein $R^4$ is hydrogen are alkylated to provide, for example, imidazobenzodiazepines 21 wherein $R^4$ is alkyl, by conventional processes. Thus, treatment of diazepinone 21 wherein $R^4$ is hydrogen with methyl iodide in dimethylformamide in the presence of sodium hydride affords the N-methylimidazobenzodiazepine 21 wherein $R^4$ is methyl.

The benzo[b]pyrrolobenzodiazepines of the present invention are useful as analgetic agents due to their ability to alleviate pain in mammals which is demonstrated in the phenyl-para-quinone writhing assay in mice, a standard assay for analgesia [Proc. Soc. Exptl. Biol. Med., 95, 729 (1953)]. Presented in the Table is the analgetic activity of representative compounds of the invention and a standard, expressed as the estimated subcutaneous dose at which the mice experience a 50% reduction in phenyl-para-quinone induced writhes, i.e., the ED$_{50}$-value, or the percent inhibition of writhing caused by a screening dose of 20 mg/kg of body weight administered subcutaneously (sc).

TABLE

| Compound | Analgetic Activity (ED$_{50}$ mg/kg) (sc) |
| --- | --- |
| 11-Bromo-1,2-dihydro-8-(dimethylamino)- | 3.55 |

TABLE-continued

| Compound | Analgetic Activity (ED$_{50}$ mg/kg) (sc) |
| --- | --- |
| methylbenzo[b]pyrrolo[3,2,1-jk][1,2,4]-triazolo[4,3-d][1,4]benzodiazepine | |
| 11-Bromo-1,2-dihydro-7-[3-(6-fluoro-1,2-benzisoxazol-3-yl)-1-propyl]benzo[b]-pyrrolo[3,2,1-jk][1,2,4]triazolo[4,3-d]-[1,4]benzodiazepin-8(7H)-one | 54% @ 20 mg/kg |
| 1,2-Dihydro-7-(2-phenylethyl)benzo[b]-pyrrolo[3,2,1-jk][1,2,4]triazolo[4,3-d]-[1,4]benzodiazepin-8(7H)-one | 62% @ 20 mg/kg |
| 11-Bromo-1,2-dihydrobenzo[b]pyrrolo-[3,2,1-jk]tetrazolo[1,5-d][1,4]benzodiazepine | 56% @ 20 mg/kg |
| 11-Methyl-8-(dimethylamino)methylbenzo[b]-pyrrolo[3,2,1-jk][1,2,4]triazolo[4,3-d]-[1,4]benzodiazepine | 57% @ 20 mg/kg |
| propoxyphene (standard) | 3.9 |

Analgesia production is achieved when the present benzo[b]pyrrolobenzodiazepines are administered to a subject requiring such treatment as an effective oral, parenteral or intravenous dose of from 0.01 to 50 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practive of the invention.

Other compounds of the invention also include:

a. 4-bromo-1,2-dihydro-8-(dimethylamino)methylbenzo[b]pyrrolo[3,2,1-jk][1,2,4]triazolo[4,3-d][1,4]benzodiazepine;

b. 4-bromo-8-(dimethylamino)methylbenzo[b]pyrrolo[3,2,1-jk][1,2,4]triazolo[4,3-d][1,4]benzodiazepine;

c. 11-chloro-1,2-dihydro-8-(dimethylamino)methylbenzo[b]pyrrolo[3,2,1-jk][1,2,4]triazolo[4,3-d][1,4]benzodiazepine;

d. 4-methyl-1,2-dihydro-8-(dimethylamino)methylbenzo[b]pyrrolo[3,2,1-jk][1,2,4]triazolo[4,3-d][1,4]benzodiazepine;

e. 11-bromo-7-[3-(6-fluoro-1,2-benzisoxazol-3-yl)-1-propyl]benzo[b]pyrrolo[3,2,1-jk][1,2,4]triazolo[4,3-d][1,4]benzodiazepin-8(7H)-one;

f. 11-methyl-1,2-dihydro-7-[3-(6-fluoro-1,2-benzisoxazol-3-yl)-1-propyl]benzo[b]pyrrolo[3,2,1-jk][1,2,4]triazolo[4,3-d][1,4]benzodiazepin8(7H)-one;

g. 7-(2-phenylethyl)benzo[b]pyrrolo[3,2,1-jk][1,2,4]triazolo[4,3-d][1,4]benzodiazepin-8(7H)-one;

h. 11-bromobenzo[b]pyrrolo[3,2,1-jk]tetrazolo[1,5-d][1,4]benzodiazepine; and i. 1,2-dihydro-11-methylbenzo[b]pyrrolo[3,2,1-jk]tetrazolo[1,5-d][1,4]benzodiazepine.

Effective amounts of the compounds of the invention may be administered to a subject by any one of various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Preferred pharmaceutically acceptable acid addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, oxalic acid and the like, and salts of tribasic carboxylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between about 4% to about 75% of the weight of the unit. The amount of present compound in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic;

The following Examples are for illustrative purposes only and are not to be construed as limiting the invention.

REACTION SCHEME A

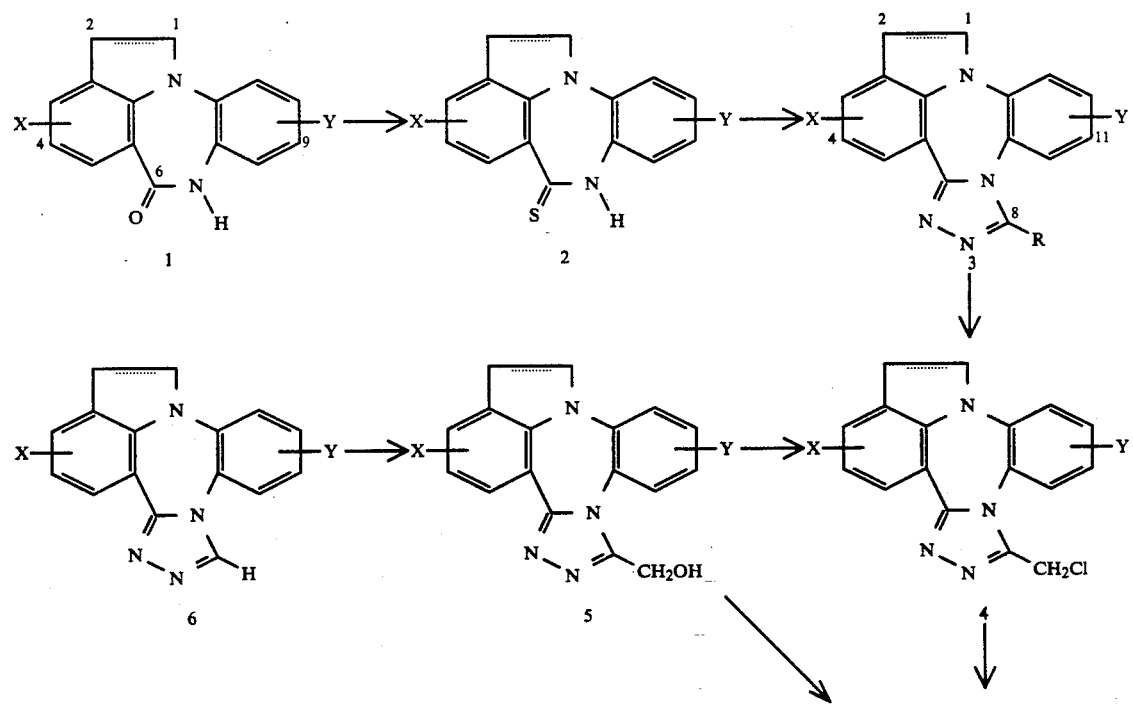

-continued
REACTION SCHEME A
wherein R, $R^6$, $R^7$, X, and Y are as hereinbefore defined
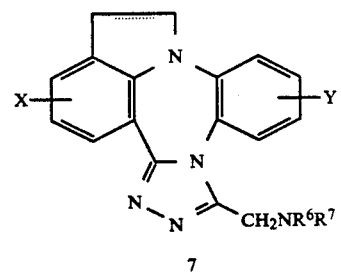
7
REACTION SCHEME B
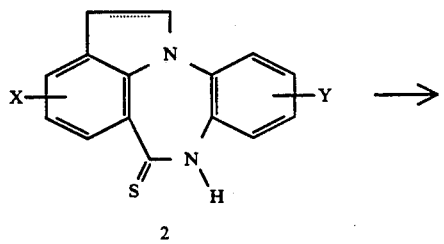
2
-continued
REACTION SCHEME B
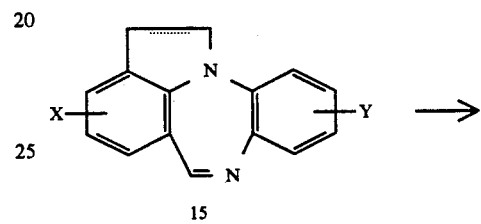
15
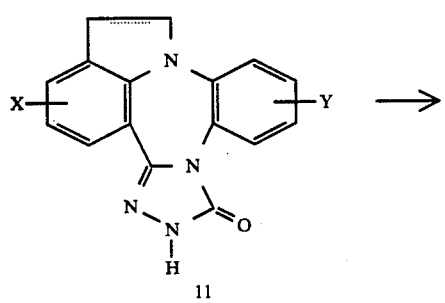
11
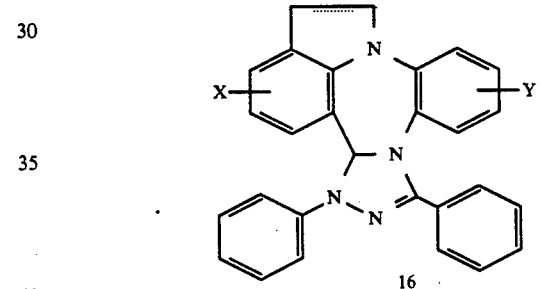
16
wherein $R^3$, X, and Y are as hereinbefore defined
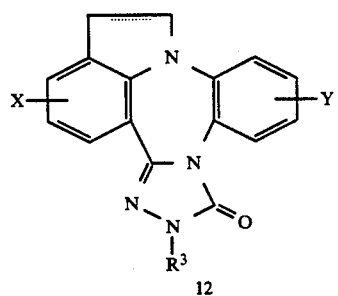
12
REACTION SCHEME C
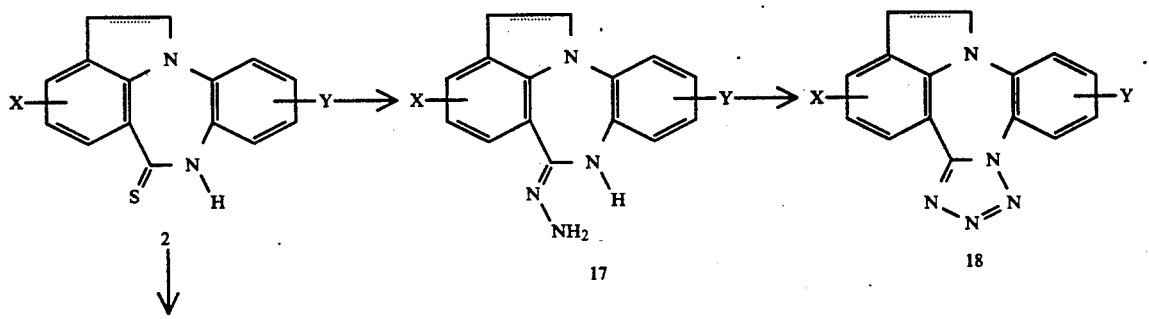

-continued
REACTION SCHEME C

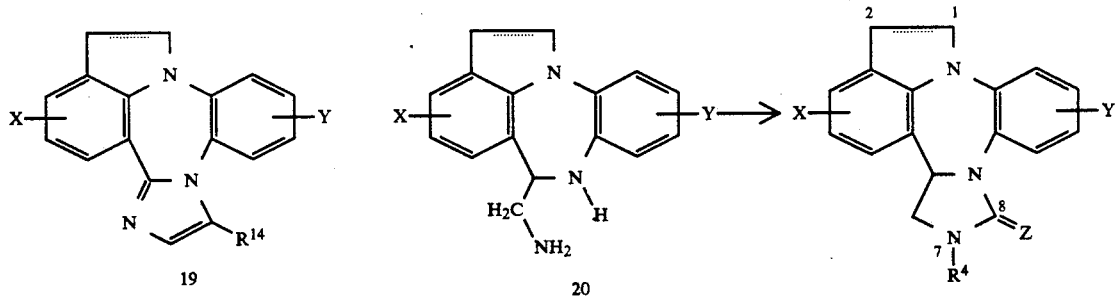

wherein R⁴, X, Y, and Z are as hereinbeforedefined and R¹⁴ is loweralkyl or benzyl

EXAMPLE 1

1,2-Dihydrobenzo[b]pyrrolo[3,2,1-jk][1,4]benzodiazepin-6-thione

To 1,2-dihydrobenzo[b]pyrrolo[3,2,1-jk][1,4]benzodiazepin-6-one (67 g) in 1 l of toluene, under nitrogen, was added 2,4-bis(4-methoxyphenyl)-1,3-dithia-2,4-diphosphetane-2,4-disulfide (45 g). The mixture was refluxed for 1 hr and allowed to stand overnight. The precipitate was collected and recrystallized from chloroform to afford 43 g, (60.2%) of product, mp 185°–186° C.

ANALYSIS: Calculated for $C_{15}H_{12}N_2S$: 70.56% C; 4.73% H; 10.85% N; Found: 70.72% C; 4.75% H; 10.96% N.

EXAMPLE 2

1,2-Dihydrobenzo[b]pyrrolo[3,2,1-jk][1,2,4]triazolo[4,3-d][1,4]benzodiazepine 1,2-Dihydrobenzo[b]pyrrolo[3,2,1-jk][1,4]benzodiazepin-6-thione (5 g), hydrazine monohydrate (5 ml) and dimethylformamide (150 ml) were combined and refluxed overnight. The reaction mixture was concentrated under reduced pressure and the residue was purified by high performance liquid chromatography (2% methanol/dichloromethane) to yield 3.5 g (68.2%) of product. Recrystallization from tetrahydrofuran gave the analytical sample, mp 177°–178° C.

ANALYSIS: Calculated for $C_{16}H_{12}N_4$: 73.82% C; 4.66% H; 21.53% N; Found: 73.81% C; 4.72% H; 21.45% N.

EXAMPLE 3

1,2-Dihydro-8-methylbenzo[b]pyrrolo[3,2,1-jk][1,2,4]triazolo[4,3-d][1,4]benzodiazepine 1,2-Dihydrobenzo[b]pyrrolo[3,2,1-jk][1,4]benzodiazepin6-thione (4.5 g), acetic hydrazide (4 g) and n-butanol (200 ml) were combined and refluxed overnight. The reaction mixture was concentrated under reduced pressure and the residue was purified by high performance liquid chromatography (2% methanol/dichloromethane) to yield 3.2 g (65%) of product. Recrystallization from ethanol gave the analytical sample, mp 237°–238° C.

ANALYSIS: Calculated For $C_{17}H_{14}N_4$: 74.42% C; 5.15% H; 20.43% N; Found: 74.43% C; 5.23% H; 20.46% N.

EXAMPLE 4

1,2-Dihydro-8-(dimethylamino)methylbenzo[b]pyrrolo3,2,1-jk][1,2,4]triazolo[4,3-d][1,4]benzodiazepine 1,2-Dihydrobenzo[b]pyrrolo[3,2,1-jk][1,4]benzodiazepin6-thione (4 g) was added to a solution of dimethylaminoacetic hydrazide hydrochloride (2 g) and triethylamine (2.4 ml) in dimethylformamide (25 ml). The mixture was refluxed overnight, cooled, and concentrated under reduced pressure. The residue was purified by high performance liquid chromatography (2.5% methanol/dichloromethane). The appropriate fractions were triturated with dry ether to yield 2.4 g (47.2%) of product, mp 164°–165° C.

ANALYSIS: Calculated for $C_{19}H_{19}N_5$: 71.89% C; 6.05% H; 22.07% N; Found: 71.88% C; 6.23% H; 21.92% N.

EXAMPLE 5

9-Bromo-1,2-dihydrobenzo[b]pyrrolo[3,2,1-jk][1,4]benzodiazepin-6-thione

To 9-bromo-1,2-dihydrobenzo[b]pyrrolo[3,2,1-jk][1,4]benzodiazepin-6-one (9 g) in toluene (175 ml), under nitrogen, was added 2,4-bis(4-methoxyphenyl)-1,3-dithia-2,4-diphosphetane-2,4-disulfide (12.6 g). The mixture was refluxed for 1 hr and concentrated under reduced pressure. Recrystallization of the residue from chloroform: hexane afforded 6 g (63%) of product, mp 196°–197° C.

ANALYSIS: Calculated for $C_{15}H_{11}BrN_2S$: 54.39% C; 3.35% H; 8.46% N; Found: 54.38% C; 3.28% H; 8.59% N.

EXAMPLE 6

11-Bromo-1,2-dihydrobenzo[b]pyrrolo[3,2,1-jk][1,2,4]triazolo[4,3-d][1,4]benzodiazepine A solution of 9-bromo-1,2-dihydrobenzo[b]pyrrolo[3,2,1-jk][1,4]benzodiazepin-6-thione (6 g) and formic hydrazide (1.1 g) in dimethylformamide (25 ml) was refluxed for 18 hrs. The reaction mixture was cooled and the precipitate was collected. The filtrate was evaporated and the residue was purified by chromatography (silica, 2% methanol/dichloromethane). The appropriate fractions were evaporated. The residues and the precipitate were combined and recrystallized from chloroform-petroleum ether to afford 2.4 g (39.4%) of product, mp 233°–234° C.

ANALYSIS: Calculated for $C_{16}H_{11}BrN_4$: 56.65% C; 3.28% H; 16.52% N; Found: 56.21% C; 3.02% H; 16.79% N.

EXAMPLE 7

11-Bromo-1,2-dihydro-8-methylbenzo[b]pyrrolo[3,2,1-jk][1,2,4]triazolo[4,3-d][1,4]benzodiazepine A stirred mixture of 9-bromo-1,2-dihydrobenzo[b]pyrrolo[3,2,1-jk][1,4]benzodiazepin-6-thione (4 g) and acetic hydrazide (2.7 g) in n-butanol (200 ml) was refluxed under nitrogen for 18 hrs. The reaction mixture was evaporated and the residue was purified by high performance liquid chromatography (2% methanol/dichloromethane) to give 2.4 g, (57%) of product. Recrystallization from ethanol gave the analytical sample mp 224°–225° C.

ANALYSIS: Calculated for $C_{17}H_{14}BrN_4$: 57.78% C; 4.00% H; 15.86% N; Found: 57.80% C; 3.80% H; 15.87% N.

EXAMPLE 8

11-Bromo-1,2-dihydrobenzo[b]pyrrolo[3,2,1-jk][1,2,4]triazolo[4,3-d][1,4]benzodiazepin8-carboxamide A mixture of 9-bromo-1,2-dihydrobenzo[b]pyrrolo[3,2,1-jk][1,4]benzodiazepin-6-thione (5 g) and oxamic hydrazide (1.56 g) in dimethylformamide (30 ml) was refluxed overnight. The reaction mixture was concentrated to 20 ml under reduced pressure and the precipitate was collected to give 2.5 g (43% yield) of product. Recrystallization from dimethylformamide provided the analytical sample, mp 287°–288° C.

ANALYSIS: Calculated for $C_{17}H_{12}BrN_5O$: 53.15% C; 2.92% H; 18.04% N; Found: 53.41% C; 3.17% H; 18.33% N.

EXAMPLE 9

11-Bromo-1,2-dihydro-8-(dimethylamino)methylbenzo[b]pyrrolo[3,2,1-jk][1,2,4]triazolo[4,3-d][1,4]benzodiazepine 9-Bromo-1,2-dihydrobenzo[b]pyrrolo[3,2,1-jk][1,4]benzodiazepin-6-thione (7 g) was added to a solution of dimethylaminoacetic hydrazide hydrochloride (3.2 g) and triethylamine (2.9 ml) in dimethylformamide (25 ml). The mixture was refluxed overnight with stirring. The reaction mixture was cooled and the precipitate was collected, washed with ether, and dried overnight under vacuum to give 7.6 g (91.6%) of product. Recrystallization from ethanol gave the analytical sample, mp 251°–252° C.

ANALYSIS: Calculated for $C_{19}H_{18}BrN_5$: 57.58% C; 4.59% H; 17.68% N; Found: 57.65% C; 4.36% H; 17.94% N.

EXAMPLE 10

11-Bromo-1,2-dihydro-8-[(4-methyl-1-piperazinyl)methyl]benzo[b]pyrrolo[3,2,1-jk][1,2,4]triazolo[4,3-d][1,4]benzodiazepine 9-Bromo-1,2-dihydrobenzo[b]pyrrolo[3,2,1-jk][1,4]benzodiazepin-6-thione (7 g) was added to a solution of N-methylpiperazine-N-acetic hydrazide (6 g) in dimethylformamide (25 ml). The mixture was refluxed overnight and cooled. The precipitate was collected, washed with ether and dried to provide 6.0 g (62%) of product. Recrystallization from 2-propanol gave the analytical sample, mp 257°–258°.

ANALYSIS: Calculated for $C_{22}H_{23}BrN_6$: 58.53% C; 5.15% H; 18.62% N; Found: 58.34% C; 5.14% H; 18.47% N.

EXAMPLE 11

11-Bromo-1,2-dihydro-8-[2-(4-methyl-1-piperazinyl)ethyl]benzo[b]pyrrolo[3,2,1-jk][1,2,4]triazolo[4,3-d][1,4]benzodiazepine 9-Bromo-1,2-dihydrobenzo[b]pyrrolo[3,2,1-jk][1,4]benzodiazepin-6-thione (4 g) was added to a solution of 4-methyl-1-piperazinylpropionic hydrazide (3.4 g) in dimethylformamide (35 ml). The reaction mixture was refluxed overnight and evaporated under reduced pressure. The residue was purified by high performance liquid chromatography (7.5% methanol/dichloromethane) to yield 2.6 g (47%) of product. Recrystallization from ethanol gave the analytical sample, mp 197°–198.5° C.

ANALYSIS: Calculated for $C_{23}H_{25}BrN_6$: 59.35% C; 5.42% H; 18.06% N; Found: 59.37% C; 5.56% H; 18.12% N.

EXAMPLE 12

1,2-Dihydro-11-methyl-8-(dimethylamino)methylbenzo[b]pyrrolo[3,2,1-jk][1,2,4]triazolo[4,3-d][1,4]benzodiazepine A mixture of 9-methyl-1,2-dihydrobenzo[b]pyrrolo[3,2,1-jk][1,4]benzodiazepin-6(7H)-thione (5.0 g) and N,N-dimethylglycine hydrazide (2.2 g) in dimethylformamide (200 ml) was refluxed for 18 hrs, under nitrogen, with stirring. The reaction mixture was evaporated, and the residue purified by high performance liquid chromatography (2.5% methanol/dichloromethane) to give 5.75 g (93.5%) of product. Recrystallization from ethyl acetate gave the analytical sample, mp 171°–172° C.

ANALYSIS: Calculated for $C_{20}H_{21}N_5$: 72.47% C; 6.40% H; 21.13% N; Found: 72.36% C; 6.40% H; 21.10% N.

EXAMPLE 13

9-Bromo-benzo[b]pyrrolo[3,2,1-jk][1,4]benzodiazepin-6(7H)-thione

A mixture of 9-bromobenzo[b]pyrrolo[3,2,1-jk][1,4]benzodiazepin-6(7H)-one (12.8 g), 2,4-bis(4-methoxyphenyl-1,3-dithia-2,4-diphosphetane-2,4-disulfide (8.3 g), and toluene (500 ml) was refluxed for 2 hrs. The reaction mixture was allowed to stand overnight at room temperature. The precipitate was collected, washed with hexane, and dried overnight under vacuum at 40° C. to provide 9.6 g, (71.5%) of product. Recrystallization from chloroform gave the analytical sample, mp 214°–215° C.

ANALYSIS: Calculated for $C_{15}H_9BrN_2S$: 54.72% C; 2.76% H; 8.51% N; Found: 54.36% C; 2.77% H; 8.41% N.

EXAMPLE 14

11-Bromo-8-(dimethylamino)methylbenzo[b]pyrrolo[3,2,1-jk][1,2,4]triazolo[4,3-d][1,4]benzodiazepine 9-Bromobenzo[b]pyrrolo[3,2,1-jk][1,4]benzodiazepin-6 (7H)-thione (5 g) was dissolved in dimethylformamide (150 ml). To this mixture was added N-dimethylglycine hydrazide (4.4 g), and the mixture was refluxed overnight. The reaction mixture was concentrated under reduced pressure, and the residue was purified by high performance liquid chromatography (2.5% methanol/dichloromethane) to give 4.8 g (65.1%) of product. Recrystallization from methanol gave the analytical sample, mp 265°–266° C.

ANALYSIS: Calculated for $C_{19}H_{16}BrN_5$: 57.87% C; 4.10% H; 17.77% N; Found: 58.03% C; 4.03% H; 17.74% N.

EXAMPLE 15

11-Methyl-8-(dimethylamino)methylbenzo[b]pyrrolo[3,2,1-jk][1,2,4]triazolo[4,3-d][1,4]benzodiazepine A mixture of 9-methylbenzo[b]pyrrolo[3,2,1-jk][1,4]benzodiazepin-6(7H)-thione (4.5 g) and N-dimethylglycine hydrazide (2.0 g) in dimethylformamide (200 ml) was refluxed for 18 hrs under nitrogen. The reaction mixture was evaporated, and the residue was purified by high performance liquid chromatography (2.5% methanol/dichloromethane) to give 3.9 g (70.1%) of product. Recrystallization from ethanol, gave the analytical sample, mp 184° C.

ANALYSIS: Calculated for $C_{20}H_{19}N_5$: 72.91% C; 5.82% H; 21.26% N; Found: 72.77% C; 5.76% H; 21.10% N.

EXAMPLE 16

11-Bromo-1,2-dihydrobenzo[b]pyrrolo[3,2,1-jk][1,2,4]triazolo[4,3-d][1,4]benzodiazepine8-methanol A mixture of 11-bromo-1,2-dihydrobenzo[b]pyrrolo[3,2,1-jk][1,2,4]triazolo[3,4-d][1,4]-benzodiazepine (25 g) in xylene (1 l) was refluxed with stirring and water collection. The solution was cooled to 125° C., and paraformaldehyde (30 g) was added slowly. The mixture was refluxed for 30 mins, cooled to 125° C. and more paraformaldehyde (10 g) was added. The mixture was refluxed for 1 hr. Additional paraformaldehyde (10 g) was added, and the mixture was refluxed for one hr. The reaction mixture was allowed to stand overnight at room temperature. The precipitate was collected, washed with ethyl acetate, and dried overnight at 40° C. under vacuum to yield 25.7 g, (94.1%) of product. Recrystallization from tetrahydrofuran/hexane gave the analytical sample, mp 222°–224°.

ANALYSIS: Calculated for $C_{17}H_{13}BrN_4O$: 55.29% C; 3.56% H; 15.18% N; Found: 55.43% C; 3.64% H; 14.98% N.

EXAMPLE 17

11-Bromo-1,2-dihydro-8-(methylamino)methylbenzo[b]pyrrolo[3,2,1-jk][1,2,4]triazolo[4,3-d][1,4]benzodiazepine A solution of methanesulfonyl chloride (0.375 g) in dichloromethane (5 ml) was added dropwise to a solution of 11-bromo-1,2-dihydrobenzo[b]pyrrolo[3,2,1-jk][1,2,4]triazolo[4,3-d][1,4]benzodiazepine-8-methanol (1.05 g) and triethylamine (0.42 g) in dichloromethane (30 ml) under nitrogen. The mixture was stirred for one hr. A solution of 40% aqueous monomethylamine (3.6 ml) was added in one portion, and the solution was stirred at room temperature for two hrs. The layers were separated. The aqueous layer was extracted with dichloromethane. The combined extracts were washed once with water and once with 10% sodium hydroxide solution, dried over anhydrous sodium sulfate and concentrated. The residue was purified by high performance liquid chromatography (5% methanol/dichloromethane) to yield 0.65 g (60.8%) of product. Recrystallization from ethyl acetate gave the analytical sample, mp 183°–184° C.

ANALYSIS: Calculated for $C_{18}H_{16}BrN_5$: 56.66% C; 4.23% H; 18.32% N; Found: 56.63% C; 4.30% H; 18.26% N.

EXAMPLE 18

11-Bromo-1,2-dihydro-N-(2-phenethyl)benzo[b]pyrrolo[3,2,1-jk][1,2,4]triazolo[4,3-d][1,4]benzodiazepine-8-methanamine A solution of methanesulfonyl chloride (1.87 g) was added dropwise to a solution of 11-bromo-1,2-dihydrobenzo[b]pyrrolo[3,2,1-jk][1,2,4]triazolo[4,3-d][1,4]benzodiazepine-8-methanol (5 g) and triethylamine (2.8 ml) in dichloromethane (250 ml) under nitrogen. The reaction mixture was stirred at room temperature for ten mins. Phenethylamine (16.4 g), was added, and the solution was stirred overnight at room temperature. The reaction mixture was washed once with water and once with dilute sodium hydroxide solution (10%). The organic extract was dried over anhydrous sodium sulfate, filtered, and evaporated. The residue was purified by high performance liquid chromatography (2% methanol/dichloromethane) to give 3.8 g, (59%) of product. Recrystallization twice from methanol gave the analytical sample, mp 187°–188° C.

ANALYSIS: Calculated for $C_{25}H_{22}BrN_5$: 63.55% C; 4.70% H; 14.83% N; Found: 63.18% C; 4.66% H; 14.68% N.

EXAMPLE 19

11-Bromo-1,2-dihydro-N-methyl-N-(2-phenylethyl)-benzo[b]pyrrolo[3,2,1-jk][1,2,4]triazolo[4,3-d][1,4]benzodiazepine-8-methanamine 11-Bromo-1,2-dihydro-8-(methylamino)methylbenzo[b]pyrrolo[3,2,1-jk][1,2,4]triazolo[4,3-d][1,4]benzodiazepine (6 g) was warmed in acetonitrile (250 ml) until a solution was obtained. Potassium carbonate (3.3 g) was added followed by phenethyl bromide (4.4 g). The reaction mixture was refluxed for 10 mins, stirred at room temperature for one hr., and filtered. The filtrate was concentrated. The residue was purified by high pressure liquid chromatography (2.5% methanol/dichloromethane) to yield 4.4 g (57.7%) of product. Recrystallization from ethanol gave the analytical sample, mp 182°–183° C.

ANALYSIS: Calculated for $C_{26}H_{24}BrN_5$: 64.19% C; 4.98% H; 14.40% N; Found: 63.99% C; 4.98% H; 14.56% N.

EXAMPLE 20

11-Bromo-1,2-dihydrobenzo[b]pyrrolo[3,2,1-jk][1,2,4]triazolo[4,3-d][1,4]benzodiazepine-8-methanamine hydrochloride Potassium phthalimide (2.14 g) was added to a solution of 11-bromo-8-chloromethyl-1,2-dihydrobenzo[b]pyrrolo[3,2,1-jk][1,2,4]triazolo[4,3-d][1,4]benzodiazepine (4 g) in dimethylformamide (30 ml). The reaction mixture was stirred for 30 mins. Chloroform was added and the mixture was poured into water. The aqueous phase was separated and extracted with chloroform. The combined chloroform extract was washed with 0.2N sodium hydroxide solution and water, dried over anhydrous sodium sulfate, filtered, and evaporated under reduced pressure. The residue was triturated with ether to give 3.2 g (59.5%) of 11-bromo-8-phthalimido-1,2-dihydrobenzo[b]pyrrolo[3,2,1-jk][1,2,4]triazolo[4,3-d][1,4]benzodiazepine.

The phthalimide was warmed in methanol (40 ml) with hydrazine hydrate (0.34 ml), with stirring, for 0.5 hr. Excess hydrochloric acid was added dropwise, with warming, and the mixture was filtered. The filtrate was concentrated, and the residue was purified by high performance liquid chromatography (7.5% methanol/dichloromethane) to yield 1.7 g (42.9%) of product. The hydrochloride was precipitated from methanolic hydrogen chloride/ether. Recrystallization from methanol gave the analytical sample, mp >285° C.

ANALYSIS: Calculated for $C_{17}H_{14}BrN_5.HCl$: 50.44% C; 3.74% H; 17.31% N; Found: 50.24% C; 3.83% H; 17.11% N.

EXAMPLE 21

11-Bromo-1,2-dihydro-N-(2-propenyl)benzo[b]pyrrol[3,2,1-jk][1,2,4]triazolo[4,3-d][1,4]benzodiazepine-8-methanamine A solution of methanesulfonyl chloride (2.24 g) was added dropwise to a mixture of 11-bromo-1,2-dihydropyrrolo[3,2,1-jk][1,2,4]triazolo[3,4-d][1,4]benzodiazepine-8-methanol (6.0 g) and triethylamine (2.5 g) in dichloromethane (300 ml) under nitrogen. The mixture was stirred at room temperature for 0.5 hr, washed with water, dilute hydrochloric acid, and dried over anhydrous sodium sulfate. The filtrate was evaporated under reduced pressure, and the residue consisting of 11-bromo-8-chloromethyl-1,2-dihydrobenzo[b]pyrrolo[3,2,1-jk][1,2,4]triazolo[4,3-d][1,4]benzodiazepine was dissolved in dimethylformamide (30 ml). Potassium iodide (600 mg) was added. The mixture was stirred for 5 mins at room temperature. Allyl amine (6 ml) was added and the mixture was stirred at room temperature overnight. The mixture was evaporated under reduced pressure, and the residue was dissolved in dichloromethane. The solution was washed with water, dilute hydrochloric acid, dried over anhydrous sodium sulfate, filtered, and evaporated under reduced pressure. The residue was purified by high performance liquid chromatography (2% methanol/dichloromethane) to provide 5.4 g (81.2%) of product. Recrystallization from methanol gave the analytical sample, mp 155° C.

ANALYSIS: Calculated for $C_{20}H_{17}BrN_5$: 58.82% C; 4.45% H; 17.15% N; Found: 58.48% C; 4.38% H; 17.04% N.

EXAMPLE 22

N-[11-bromo-1,2-dihydrobenzo[b]pyrrolo[3,2,1-jk][1,2,4]triazolo[4,3-d][1,4]benzodiazepin-8-yl]methyl-N-methylcyclopropane carboxamide 11-Bromo-1,2-dihydro-8-(methylamino)methyl)benzo[b]pyrrolo[3,2,1-jk][1,2,4]triazolo[4,3-d][1,4]benzodiazepine (6 g) was dissolved with warming in acetonitrile (250 ml). Potassium carbonate (3.3 g) was added followed by cyclopropanecarboxylic acid chloride (2.5 g). The reaction mixture was refluxed for one hr, stirred overnight at room temperature, filtered, and the filtrate was concentrated under reduced pressure. The residue was purified by high performance liquid chromatography (2.5% methanol/dichloromethane) to yield 4.5 g (64%) of product, which solidified upon trituration with ether. Recrystallization from ethyl acetate/hexane gave the analytical sample, mp 166°-167° C.

ANALYSIS: Calculated for $C_{22}H_{20}BrN_5O$: 58.66% C; 4.49% H; 15.55% N; Found: 58.40% C; 4.54% H; 15.53% N.

EXAMPLE 23

11-Bromo-1,2-dihydro-N-cyclopropylmethylbenzo[b]pyrrolo[3,2,1-jk][1,2,4]triazolo[4,3-d][1,4]benzodiazepine-8-methanamine A solution of methanesulfonyl chloride (1.46 g) was added dropwise to a mixture of 11-bromo-1,2-dihydrobenzo[b]pyrrolo[3,2,1-jk][1,2,4]triazolo[4,3-d][1,4]benzodiazepine- 8-methanol (4 g), and triethylamine (1.65 g) in dichloromethane (250 ml) under nitrogen. The mixture was stirred at room temperature for 30 mins, washed with water, dilute hydrochloric acid, and dried over anhydrous sodium sulfate. The mixture was evaporated under reduced pressure, and the residue was dissolved in dimethylformamide. Potassium iodide (400 mg) was added and the mixture was stirred for 5 mins at room temperature. Cyclopropylmethylamine (1.5 g) was added in one portion, and the mixture was stirred overnight at room temperature. The mixture was evaporated under reduced pressure, and the residue was dissolved in dichloromethane. The solution was washed with water, dilute hydrochloric acid, and the organic layer was dried over anhydrous sodium sulfate and filtered. The filtrate was purified by high performance liquid chromatography (2.5% methanol/dichloromethane) to yield 2.7 g (58.7%) of product, which solidified on trituration with ether. Recrystallization from tetrahydrofuran gave the analytical sample, mp 197°-198° C.

ANALYSIS: Calculated for $C_{21}H_{20}BrN_5$: 59.71% C; 4.78% H; 16.59% N; Found: 59.53% C; 4.88% H; 16.41% N;

EXAMPLE 24

1,2,5a,6-Tetrahydro-6,8-diphenylbenzo[b]pyrrolo[3,2,1-jk][1,2,4]triazolo-[4,3-d][1,4]benzodiazepine hemiethanolate To a solution of 1,2-dihydrobenzo[b]pyrrolo[3,2,1-jk][1,4]-benzodiazepine (5 g) and benzphenylhydrazidoyl chloride (5.2 g) in benzene (100 ml), was added a solution of triethylamine (4.7 ml) in benzene, with stirring. The reaction mixture was refluxed overnight and was washed with water and concentrated in vacuo. The residue was purified by high performance liquid chromatography (2% methanol/dichloromethane) to give 8 g (85.5%) of product. Recrystallization from ethanol gave the analytical sample, mp 156°-157° C.

ANALYSIS: Calculated for $C_{28}H_{22}N_4.0.5C_2H_6O$: 79.59% C; 5.77% H; 12.80% N; Found: 79.23% C; 5.55% H; 12.66% N;

EXAMPLE 25

7-(Cyclopropylmethyl)-1,2-dihydrobenzo[b]pyrrolo[3,2,1-jk][1,2,4]triazolo-[4,3-d][1,4]benzodiazepin-8-(7H)-one 1,2-Dihydrobenzo[b]pyrrolo[3,2,1-jk][1,2,4]triazolo[4,3-d][1,4]benzodiazepin-8(7H)-one (5.2 g) was dissolved in dimethylformamide (150 ml). Potassium carbonate (0.5 g) was added, followed by (chloromethyl)cyclopropane (2.1 ml). The mixture was stirred at 95° C. overnight, filtered, and evaporated under reduced pressure. The residue was purified by high performance liquid chromatography (1% methanol/dichloromethane) to yield 3.4 g (54.8%) of product. Recrystallization from pentane/ether gave the analytical sample, mp 99° C.

ANALYSIS: Calculated for $C_{20}H_{18}N_4O$: 72.69% C; 5.50% H; 16.96% N; Found: 72.87% C; 5.54% H; 16.93% N.

EXAMPLE 26

1,2-Dihydro-7-(2-phenylethyl)benzo[b]pyrrolo[3,2,1-jk][1,2,4]triazolo-[4,3-d][1,4]benzodiazepin-8(7H)-one 1,2-Dihydrobenzo[b]pyrrolo[3,2,1-jk][1,2,4]triazolo-[4,3-d][1,4]benzodiazepin-8(7H)-one (2 g) was dissolved in dimethylformamide (50 ml). Potassium carbonate (0.5 g) was added followed by (2-bromoethyl)benzene (2.7 g). The mixture was stirred at 95° C. overnight, filtered, and the filtrate was evaporated under reduced pressure. The residue was purified by high performance liquid chromatography (2% methanol/dichloromethane) to yield 2.3 g, (84%) of product. Recrystallization from methanol gave the analytical sample, mp 157°–158° C.

ANALYSIS: Calculated for $C_{24}H_{20}N_4O$: 75.76% C; 5.31% H; 14.73% N; Found: 75.80% C; 5.27% H; 14.63% N;

EXAMPLE 27

1,2-Dihydro-7-(2-propenyl)benzo[b]pyrrolo[3,2,1-jk][1,2,4]triazolo[4,3-d][1,4]benzodiazepin-8(7H)-one 1,2-dihydrobenzo[b]pyrrolo[3,2,1-jk][1,2,4]triazolo[4,3-d][1,4]benzodiazepin-8(7H)-one (2.5 g) was dissolved in dimethylformamide (50 ml). Potassium carbonate (0.5 g) was added followed by allyl bromide (2.2 g). The reaction mixture was stirred at 95° C. overnight, filtered, and the filtrate was concentrated under reduced pressure. The residue was purified by high performance liquid chromatography (2% methanol/dichloromethane) to yield 1.9 g (65.9%) of product. Recrystallization from methanol gave the analytical sample, mp 109°–110° C.

ANALYSIS: Calculated for $C_{19}H_{16}N_4O$: 72.12% C; 5.11% H; 17.71% N; Found: 72.02% C; 4.98% H; 17.61% N.

EXAMPLE 28

11-Bromo-1,2-dihydrobenzo[b]pyrrolo[3,2,1-jk][1,2,4]triazolo[4,3-d][1,4]benzodiazepin-8(7H)-one 9-Bromo-1,2-dihydrobenzo[b]pyrrolo[3,2,1-jk][1,4]-benzodiazepine-6-thione (10 g) was added to ethyl carbazate (31.3 g). The mixture was stirred 1 hr in an oil bath maintained at 195°–200° C., with condensate collection. Approximately 20 ml of condensate was collected. The mixture was cooled and 200 ml of water was added. The suspension was filtered, and the filter cake was dried overnight at 44° C. under vacuum. The filter cake was crystallized from dimethylformamide to give 8.1 g (76%) of product. Recrystallization from dimethylformamide-magnesium sulfate gave the analytical sample, mp > 300° C.

ANALYSIS: Calculated for $C_{16}H_{11}BrN_4O$: 54.10% C; 3.13% H; 15.78% N; Found: 54.01% C; 3.16% H; 15.90% N.

EXAMPLE 29

11-Bromo-1,2-dihydro-7-[2-(dimethylamino)ethyl]benzo[b]pyrrolo[3,2,1-jk][1,2,4]triazolo[4,3-d][1,4]benzodiazepin-8(7H)-one hydrochloride 11-Bromo-1,2-dihydrobenzo[b]pyrrolo[3,2,1-jk][1,2,4]triazolo[4,3-d][1,4]benzodiazepin-8(7H)-one (3.0 g) was dissolved in dimethylformamide (100 ml). Sodium hydride (1.2 g, 50% oil dispersion) was added, and the solution was heated to 95° C. for 1.5 hrs. The reaction mixture was cooled to 50° C., and a mixture of 2-dimethylaminoethyl chloride hydrochloride (1.33 g) in xylene (1.33 g) was added, with stirring. The reaction mixture was stirred for 18 hrs at 95° C., cooled to room temperature, filtered, and the filtrate was concentrated under reduced pressure. The residue was purified by high pressure liquid chromatography (1% methanol/dichloromethane) to give 2.5 g (69%) of product. The hydrochloride was precipitated from methanolic hydrogen chloride. Two recrystallizations from methanol gave the analytical sample, mp 285° C.

ANALYSIS: Calculated for $C_{20}H_{20}BrN_5O \cdot HCl$: 51.90% C; 4.58% H; 15.14% N; Found: 51.83% C; 4.76% H; 14.92% N.

EXAMPLE 30

11-Bromo-1,2-dihydro-7-[3-(dimethylamino)propyl]-benzo[b]pyrrolo[3,2,1-jk][1,2,4]triazolo[4,3-d][1,4]benzodiazepin-8(7H)-one hydrochloride hemihydrate 11-Bromo-1,2-dihydrobenzo[b]pyrrolo[3,2,1-jk][1,2,4]triazolo[4,3-d][1,4]benzodiazepine-8(7H)-one (2.5 g) was dissolved in dimethylformamide (150 ml). Sodium hydride (1.0 g, 50% oil dispersion) was added, and the solution was heated to 95° C. for 1.5 hrs. 3-Dimethylaminopropyl chloride (1.0 g) was added in one portion. The reaction mixture was stirred for 18 hrs at 95° C., filtered, and the filtrate was concentrated under reduced pressure. The residue was purified by high performance liquid chromatography (1% methanol/dichloromethane) to give 2.2 g (71.3%) of product. The hydrochloride was prepared using methanolic hydrogen chloride. Two recrystallizations from absolute ethanol gave the analytical sample, mp 245° C.

ANALYSIS: Calculated for $C_{21}H_{22}BrN_5O \cdot HCl \cdot 0.5 H_2O$: 51.91% C; 4.99% H; 14.42% N; Found: 51.39% C; 4.90% H; 14.43% N.

EXAMPLE 31

11-Bromo-1,2-dihydro-7-[3-(2-methyl-1H-indol-3-yl)propyl]benzo[b]pyrrolo[3,2,1-jk][1,2,4]triazolo[4,3-d][1,4]benzodiazepin-8(7H)-one A mixture of 11-bromo-1,2-dihydrobenzo[b]pyrrolo[3,2,1-jk][1,2,4]triazolo[4,3-d][1,4]benzodiazepin-8(7H)-one (5 g), 3-(2-methyl-1H-indol-3-yl)propyl sulfonate (5.4 g), potassium carbonate (3 g), and dimethylformamide (50 ml) was heated at 100° C. overnight, with stirring. The reaction mixture was filtered, and the filtrate was concentrated under reduced pressure. The residue was purified by high performance liquid chromatography (1% methanol/dichloromethane) to give 4.3 g (58.5%) of product. Recrystallization from methanol gave the analytical sample, mp 139°–141° C.

ANALYSIS: Calculated for $C_{28}H_{24}BrN_5O$: 63.99% C; 4.61% H; 13.33% N; Found: 63.77% C; 4.61% H; 13.40% N.

EXAMPLE 32

11-Bromo-1,2-dihydro-7-[3-(6-fluoro-1,2-benzisoxazol-3-yl)-1-propyl]benzo[b]pyrrolo[3,2,1-jk][1,2,4]triazolo[4,3-d][1,4]benzodiazepin-8(7H)-one A mixture of 11-bromo-1,2-dihydrobenzo[b]pyrrolo[3,2,1-jk][1,2,4]triazolo[4,3-d][1,4]benzodiazepin-8(7H)-one (5 g), 3-(3-chloropropyl)-6-fluoro-1,2-benzisoxazole (3.62 g), potassium carbonate (3 g), and dimethylformamide (50 ml) was heated at 100° C. overnight, with stirring. The reaction mixture was filtered, and the filtrate was concentrated under reduced pressure. The residue was purified by high performance liquid chromatography (1% methanol/dichloromethane) to yield 5.3 g (70.5%) of product. Recrystallization from methanol gave the analytical sample, mp 111°–112° C.

ANALYSIS: Calculated for $C_{26}H_{19}BrFN_5O_2$: 58.65% C; 3.60% H; 13.16% N; Found: 58.60% C; 3.55% H; 13.03% N.

EXAMPLE 33

11-Bromo-1,2-dihydro-7-[4,4-bis(4-fluorophenyl)butyl]-benzo[b]pyrrolo[3,2,1-jk][1,2,4]triazolo[4,3-d][1,4]benzodiazepin-8(7H)-one A mixture of 11-bromo-1,2-dihydrobenzo[b]pyrrolo[3,2,1-jk][1,2,4]triazolo[4,3-d][1,4]benzodiazepin-8(7H)-one (5 g), 4-chloro-1,1-bis (4-fluorophenyl)butane (5.2 g), potassium carbonate(5.2 g), and dimethylformamide (50 ml) was heated at 100° C. overnight, with stirring. The reaction mixture was cooled, filtered, and the filtrate was concentrated under reduced pressure. The residue was purified by high performance liquid chromatography (2% methanol/dichloromethane) to give 6.9 g, (81.6%) of product. Recrystallization from ethanol gave the analytical sample, mp 129°–131° C.

ANALYSIS: Calculated for $C_{32}H_{26}BrF_2N_4O$: 64.00% C; 4.37% H; 9.33% N; Found: 64.09% C; 4.13% H; 9.41% N;

EXAMPLE 34

9-Bromo-6-hydrazono-1,2,6,7-tetrahydrobenzo[b]pyrrolo[3,2,1-jk][1,4]benzodiazepine 9-Bromo-1,2-dihydrobenzo[b]pyrrolo[3,2,1-jk][1,4]benzodiazepin-6-thione (4 g), hydrazine hydrate (4 ml) and benzene (150 ml) were combined and refluxed overnight. The reaction mixture was concentrated to approximately 50 ml and, after standing overnight, the precipitate was filtered. Recrystallization of the filter cake from chloroform/ether gave 2.35 g (59.5%) of product, mp 260° C. (dec).

ANALYSIS: Calculated for $C_{15}H_{13}BrN_4$: 54.72% C; 3.99% H; 17.02% N; Found: 54.46% C; 4.06% H; 16.81% N.

EXAMPLE 35

11-Bromo-1,2-dihydrobenzo[b]pyrrolo[3,2,1-jk]tetrazolo[1,5-d][1,4]benzodiazepine 9-Bromo-6-hydrozono-1,2,6,7-tetrahydrobenzo[b]pyrrolo[3,2,1-jk][1,4]benzodiazepine (2.2 g) and sodium nitrite (2.3 g) were combined and 2N hydrochloric acid (25 ml) was added dropwise at room temperature, with stirring. After two hrs, the reaction mixture was filtered, and the filter cake was washed with water several times and dried overnight under vacuum. Recrystallization from dimethylformamide gave 1 g (43.9%) of product, mp 239°–240° C.

ANALYSIS: Calculated for $C_{15}H_{10}BrN_5$: 52.95% C; 2.97% H; 20.59% N; Found: 52.39% C; 2.81% H; 20.25% N.

EXAMPLE 36

1,2,5b,6-Tetrahydrobenzo[b]imidazo[3,4-d]pyrrolo[3,2,1-jk][1,4]benzodiazepin-8(7H)-one 6-Aminomethyl-1,2,6,7-tetrahydrobenzo[b]pyrrolo[3,2,1-jk][1,4]benzodiazepine (6 g) was dissolved in dichloromethane (600 ml). Potassium carbonate was added and the solution was cooled to 0° C. Phosgene (18.72 g of a 12.5% solution by weight in benzene) was added. The reaction mixture was stirred for 2 hrs at low temperature. The solution was diluted to 1.5 l with dichloromethane, and the solution was washed with water, brine, dried over anhydrous magnesium sulfate, and filtered. The filtrate was concentrated under reduced pressure. The residue was purified by flash chromatography over silica gel (80 g, eluted with 1% methanol/dichloromethane). Two recrystallizations of the appropriate fractions from methanol afforded 1.7 g (25.7%) of product, mp 264°–265° C.

ANALYSIS: Calculated for $C_{17}H_{15}N_3O$: 73.61% C; 5.46% H; 15.15% N; Found: 73.14% C; 5.55% H; 15.10% N.

EXAMPLE 37

1,2,5b,6-Tetrahydro-7-methylbenzo[b]imidazo[3,4-d]pyrrolo[3,2,1-jk][1,4]benzodiazepin-8(7H)-one 1,2,6,7-Tetrahydrobenzo[b]imidazo[3,4-d]pyrrolo[3,2,1-jk][1,4]benzodiazepin-8-(7H)-one (2.5 g) was dissolved in dimethylformamide (150 ml) and the solution was cooled to 0° C. Sodium hydride (0.45 g, 50% oil dispersion) was added. The reaction mixture was stirred for 3 hrs at low temperature and methyl iodide (0.62 ml) was added dropwise. The reaction was stirred for 3 hrs. The solution was diluted to 1 l with dichloromethane, washed with water, brine, dried over anhydrous magnesium sulfate, and filtered. The filtrate was concentrated under reduced pressure. The residue was purified by flash chromatography over silica gel (50 g, eluted with dichloromethane) to give 1.92 g (73%) of product. Two recrystallizations from ethanol gave the analytical sample, mp 237°–238° C.

ANALYSIS: Calculated for $C_{18}H_{17}N_3O$: 74.19% C; 5.89% H; 14.42% N; Found: 74.00% C; 5.88% H; 14.18% N.

EXAMPLE 38

1,2,5b,6-Tetrahydrobenzo[b]imidazo[3,4-d]pyrrolo[3,2,1-jk][1,4]benzodiazepin8(7H)-thione 6-Aminomethyl-1,2,6,7-tetrahydrobenzo[b]pyrrolo[3,2,1-jk][1,4]benzodiazepine (1 g) was dissolved in 95% ethanol (100 ml). Carbon disulfide (2 ml) was added, and the solution was refluxed for 5 hrs. The reaction mixture was filtered and the filter cake was washed with 95% ethanol to give 0.9 g (77.2%) of product. Recrystallization from absolute ethanol gave the analytical sample, mp 267°–269° C. (dec).

ANALYSIS: Calculated for $C_{17}H_{15}N_3S$: 69.59% C; 5.16% H; 14.32% N; Found: 69.41% C; 5.07% H; 14.59% N.

EXAMPLE 39

1,2-Dihydro-8-methylbenzo[b]imidazo[1,2-d]pyrrolo[3,2,1-jk][1,4]benzodiazepine 1,2-Dihyrobenzo[b]pyrrolo[3,2,1-jk][1,4]benzodiazepin-6-thione (4 g), propargylamine (1.2 ml), n-butanol (100 ml) and a catalytic amount of p-toluenesulfonic acid were combined and refluxed overnight. The reaction mixture was concentrated under reduced pressure. The residue was purified by high performance liquid chromatography (2% methanol/dichloromethane) to give 3.1 g (71.4%) of product. Recrystallization from ethanol gave the analytical sample, mp 175° C.

ANALYSIS: Calculated for $C_{18}H_{15}N_3$: 79.08% C; 5.54% H; 15.37% N; Found: 79.27% C; 5.49% H; 15.35% N.

EXAMPLE 40

11-Bromo-1,2-dihydro-8-methylbenzo[b]imidazo[1,2-d]pyrrolo[3,2,1-jk][1,4]benzodiazepine A mixture of 9-bromo-1,2-dihydrobenzo[b]pyrrolo[3,2,1-jk][1,4]benzodiazepin-6-thione (5.0 g), propargylamine (2.0 ml), p-toluenesulfonic acid (100 mg), and butanol (100 ml) was refluxed overnight under nitrogen, with stirring. The reaction mixture was evaporated. The residue was purified by flash column chromatography (100 g silica, eluted with dichloromethane) to give 3.2 g (60%) of product. Recrystallization from ethanol gave the analytical sample, mp 194°–196° C.

ANALYSIS: Calculated for $C_{18}H_{14}BrN_3$: 61.53% C; 4.02% H; 11.96% N; Found: 61.42% C; 4.02% H; 12.18% N.

We claim:

1. A process for the preparation of a compound of the formula

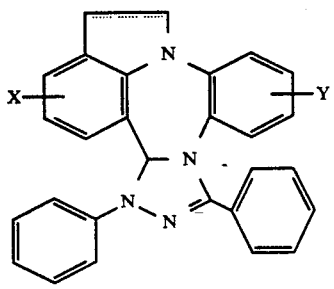

wherein X and Y are independently hydrogen, loweralkyl, or halogen; and the dotted line represents an optional carbon-to-carbon bond which comprises contacting a compound of the formula

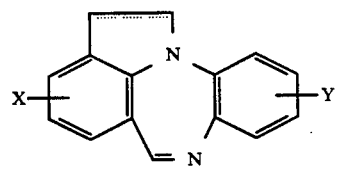

wherein X and Y and the dotted line are as above with bis-phenylhydrazidoyl chloride.

2. The process of claim 1 wherein an aromatic solvent is employed.

3. The process of claim 2 wherein the aromatic solvent is benzene, toluene, or xylene.

4. The process of claim 3 wherein the aromatic solvent is benzene.

5. The process of claim 1 wherein an acid acceptor is employed.

6. The process of claim 5 wherein the acid acceptor is a trialkylamine.

7. The process of claim 6 wherein the trialkylamine is trimethylamine, triethylamine, or tri-(2-propyl)amine.

8. The process of claim 7 wherein the trialkylamine is triethylamine.

9. A process for the preparation of a compound of the formula

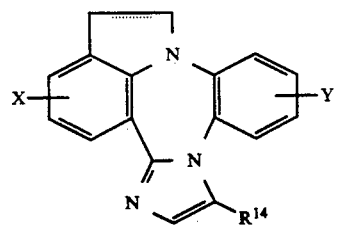

wherein $R^{14}$ is loweralkyl, or benzyl; X and Y are independently hydrogen, loweralkyl, or halogen; and the dotted line represents an optional carbon-to-carbon bond, which comprises contacting a compound of the formula

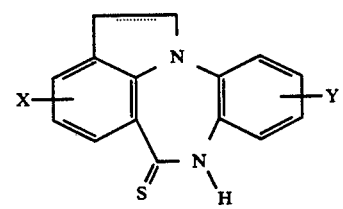

wherein X and Y and the dotted line are as above with a compound of the formula $$R^{14}-C\equiv C-CH_2NH_2$$

wherein $R^{14}$ is hydrogen, loweralkyl, or phenyl.

10. The process of claim 9 wherein a solvent is employed.

11. The process of claim 10 wherein the solvent is an alkanol.

12. The process of claim 11 wherein the alkanol is methanol, ethanol, 2-propanol, or 1-butanol.

13. The process of claim 12 wherein the alkanol is methanol.

14. The process of claim 9 wherein an organic acid is employed.

15. The process of claim 14 wherein the organic acid is a sulfonic acid.

16. The process of claim 15 wherein the sulfonic acid is methane sulfonic acid or para-toluenesulfonic acid.

17. The process of claim 16 wherein the sulfonic acid is para-toluenesulfonic acid.

18. A process for the preparation of a compound of the formula

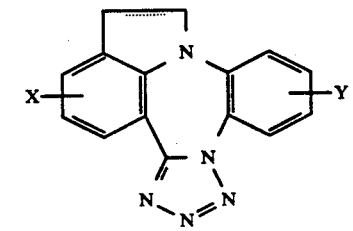

wherein X and Y are independently hydrogen, loweralkyl, or halogen; and the dotted line represents an optional carbon-to-carbon bond, which comprises contacting a compound of the formula

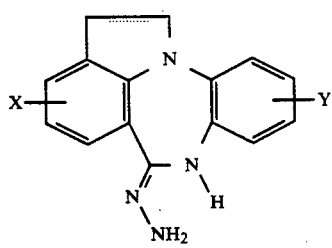

wherein X and Y and the dotted line are as above with an alkali metal nitrite and a mineral acid.

19. The process of claim 18 wherein the alkali metal nitrite is sodium nitrite or potassium nitrite.

20. The process of claim 19 wherein the alkali metal nitrite is sodium nitrite.

21. The process of claim 18 wherein the mineral acid is hydrochloric acid or hydrobromic acid.

22. The process of claim 21 wherein the mineral acid is hydrochloric acid.

* * * * *